(12) United States Patent
Wu et al.

(10) Patent No.: US 10,774,307 B2
(45) Date of Patent: Sep. 15, 2020

(54) METHOD OF INDUCING AND DIFFERENTIATING HUMAN SKIN-DERIVED PRECURSORS TO DIFFERENTIATE INTO CORNEAL ENDOTHELIAL-LIKE CELLS

(71) Applicant: Xinyi Wu, Jinan Shandong (CN)

(72) Inventors: Xinyi Wu, Jinan Shandong (CN); Lin Shen, Jinan Shandong (CN)

(73) Assignee: Xinyi Wu, Jinan Shandong (CN)

( * ) Notice: Subject to any disclaimer, the term of this patent is extended or adjusted under 35 U.S.C. 154(b) by 46 days.

(21) Appl. No.: 15/719,585

(22) Filed: Sep. 29, 2017

(65) Prior Publication Data
US 2018/0105796 A1 Apr. 19, 2018

(30) Foreign Application Priority Data
Oct. 13, 2016 (CN) .......................... 2016 1 0894664

(51) Int. Cl.
*C12N 5/079* (2010.01)
*A61L 27/38* (2006.01)
*A61L 27/36* (2006.01)

(52) U.S. Cl.
CPC ........ *C12N 5/0621* (2013.01); *A61L 27/3604* (2013.01); *A61L 27/3808* (2013.01); *A61L 27/3839* (2013.01); *A61L 2430/16* (2013.01); *C12N 2500/30* (2013.01); *C12N 2500/90* (2013.01); *C12N 2501/115* (2013.01); *C12N 2502/09* (2013.01); *C12N 2506/09* (2013.01); *C12N 2509/00* (2013.01)

(58) Field of Classification Search
CPC .............. C12N 5/0621; C12N 2500/30; C12N 2500/90; C12N 2501/115; C12N 2502/09; C12N 2506/09; C12N 2509/00; A61L 27/3839; A61L 27/3808; A61L 27/3604; A61L 2430/16
See application file for complete search history.

(56) References Cited

U.S. PATENT DOCUMENTS

| 2003/0003574 | A1* | 1/2003 | Toma ................... | C12N 5/0607 435/368 |
| 2009/0053809 | A1* | 2/2009 | Zander .................. | C12N 5/062 435/377 |
| 2010/0239640 | A1* | 9/2010 | Miller ................... | A61K 35/36 424/443 |
| 2012/0009645 | A1* | 1/2012 | Oh ........................ | C12N 5/0606 435/176 |
| 2014/0314723 | A1* | 10/2014 | Yim ..................... | C12N 5/0621 424/93.7 |
| 2014/0315305 | A1* | 10/2014 | Shimmura .......... | A61L 27/3808 435/377 |

FOREIGN PATENT DOCUMENTS

CN 101638635 A * 2/2010 ............... C12N 5/08
CN 101638635 A 2/2010

OTHER PUBLICATIONS

OpenWetWare, https://openwetware.org/wiki/TissueCulture:Thawing_cells, 2012, pp. 1-3. (Year: 2012).*
Machine translation for CN 101638635 A, publication date Feb. 3, 2010, pp. 1-25. (Year: 2010).*
Chengqun Ju et al.,"Derivation of Corneal Endothelial Cell-Like Cells from Rat Neural Crest Cells In Vitro",PLoS ONE, vol. 7,No. 7,Dec. 31, 2012.
Karl J. L. Fernandes et a.,"A dermal niche for multipotent adult skin-derived precursor cells",Nature Cell Biology,vol. 6,No. 11,Dec. 31, 2004.
Guiying Liu et al.,"Phenotypes and characteristics of human skin-derived precursors",Chinese Journal of Tissue Engineering Research,vol. 17, No. 36,Sep. 3, 2013, abstract only.

* cited by examiner

*Primary Examiner* — Taeyoon Kim
(74) *Attorney, Agent, or Firm* — Wayne & Ken, LLC; Tony Hom

(57) ABSTRACT

The present invention discloses a method of inducing and differentiating human skin-derived precursors into corneal endothelial-like cells. The present invention utilizes human skin-derived precursors to induce corneal endothelial-like cells that are theoretically close to normal human corneal endothelial cells successfully by co-culturing with B4G12 corneal endothelial cells. Furthermore, the obtained corneal endothelial-like cells are applied to a corneal endothelial decompensation animal model, and corneal endothelium of the animal is successfully repaired, which has an important clinical application prospect.

5 Claims, 7 Drawing Sheets

METHOD OF INDUCING AND DIFFERENTIATING HUMAN SKIN-DERIVED PRECURSORS TO DIFFERENTIATE INTO CORNEAL ENDOTHELIAL-LIKE CELLS

TECHNICAL FIELD

The present invention relates to a method of inducing and differentiating human skin-derived precursors to differentiate into corneal endothelial-like cells, and belongs to the technical field of tissue engineering and ophthalmic reconstruction.

BACKGROUND

In five layers of cornea structure, endodermis located in the innermost layer has great significance on maintaining corneal transparency and normal corneal physiological function. Human Corneal Endothelial Cells (HCECs) regulate the transparency of cornea through pump function and barrier function. However, since adult corneal endothelial cells lack proliferation ability, its cytothesis mainly relies on cellular extension and migration of surrounding cells after damage. Corneal endothelial decompensation can be induced when the cell density is less than 500-800/mm$^2$, leading to corneal edema and to losing transparency. Infection, inflammation, trauma, eye surgery and etc. may all induce endothelial cell damage, but due to the special physiological properties of human corneal endothelial cells, endothelial cell function recovery is often a difficult problem for eye disease treatment. The only effective way to treat corneal endothelial decompensation is to transplant corneal endothelial cells from a healthy donor and to replace the damaged or pathological changed cells by penetrating corneal transplantation or corneal endothelial transplantation. Given to worldwide extreme lack of available donor for corneal transplantation, and to postoperative immunological rejection, the application of corneal transplantation has been limited. Biological corneal transplantation can effectively relieve the pressure of natural corneal materials and has great value socially and economically. However, it demands sufficient supply of corneal endothelial cells for the purpose of the construction of biological corneal endothelial as well as merely endothelial cells transplantation. Due to limited proliferative capacity of adult corneal endothelial cells as well as the limited ability of external culture amplification, to find new endothelial cells is an urgent problem to be solved. It is extremely urgent to obtain a large number of functional coneal endothelial cells similar to normal human to meet the needs for cytobiology research and cell replacement therapy.

At present, research on the inducting differentiation of corneal endothelial cells is still in its early stage. Researchers earlier have tried to replace non-proliferable corneal endothelial cells with adipose skin cells or mesenchymal stem cells or tried to induce differentiation of embryonic stem cells, stromal stem cells, bone marrow endothelial progenitor cells or neural crest cells into corneal endothelial cells, but these methods all exist some problems, such as immune rejection, ethical issues, poor histocompatibility and lack of animal experiments, etc. A method for achieving a large number of functional corneal endothelial cells in vitro has not been found yet.

SUMMARY

Given to existing problems of the prior art, the present invention provides a method of inducing and differentiating human Skin-derived Precursors (SKPs) into human corneal endothelial cells. The present invention utilizes human skin-derived precursors to induce corneal endothelial-like cells that are theoretically close to normal human corneal endothelial cells successfully by co-culturing with B4G12 corneal endothelial cells. Furthermore, the obtained corneal endothelial-like cells are applied to a corneal endothelial decompensation animal model, and corneal endothelium of the animal is successfully repaired, which has an important clinical application prospect.

The first purpose of the present invention is to provide a method of inducing and differentiating human skin-derived precursors into corneal endothelial-like cells.

The second purpose of the present invention is to provide corneal endothelial-like cells.

The third purpose of the present invention is to provide an application of the obtained corneal endothelial-like cells.

The fourth purpose of the present invention is to provide a corneal transplantation of the above described corneal endothelial-like cells.

The purposes of the present invention are realized by following technical scheme:

A method of inducing and differentiating human Skin-derived Precursors (SKPs) into corneal endothelial cells adopts co-culturing human skin-derived precursors with human corneal endothelial cells, and induces and differentiate human skin-derived precursors into corneal endothelial-like cells.

Firstly, the present invention directly adopts human Skin-derived Precursors (SKPs) to induce, in order to avoid immune rejection, ethical issues, poor histocompatibility, etc., which is more beneficial for future clinical application. Moreover, the purpose of utilizing human skin-derived precursors is that neuron-like cells are merely occasionally seen in random differentiation cells from human skin-derived precursors in vitro, but mice skin-derived precursors are easy to be differentiated into typical nerve cells, illustrating that human skin-derived precursors are not completely the same as that of mice under the same culture conditions (Liu et al., "Phenotype And Characteristic Of Human Skin-Derived Precursors", <China Tissue Engineering Research>, vol 17, period 36). Adopting mice skin-derived precursors cannot solve the problems of demand on corneal endothelial-like cells.

Secondly, the present invention adopts induction in a manner of co-culturing human skin-derived precursors and corneal endothelial-like cells. It avoids the cytotoxicity induced by adopting cytokines and chemical inductive agent, which is more favorable to clinical experiments and application. The present invention certifies for the first time that induction in the manner of co-culturing of human skin-derived precursors and corneal endothelial-like cells can produce corneal endothelial-like cells.

Human corneal endothelial cells, preferably, are B4G12 human corneal endothelial cell lines. Selecting these cells can avoid complex procedures of extracting primary human corneal endothelial cells and avoid over-demand on human corneal endothelial cells. These cell lines are commercialized and easy to be prepared and cultured in a large scale, which is more convenient for commercialized production.

The manner of co-culturing human skin-derived precursors and human corneal endothelial-like cells, preferably, is non-contact co-culturing manner; one of the manners adopted, preferably, is transwell chamber for non-contact co-culturing.

The method described specifically comprises the following steps:

Step 1: culturing of human Skin-derived Precursors (SKPs);
Step 2: culturing of corneal endothelial cells B4G12, and
Step 3: induction of corneal endothelial-like cells;

The culturing manner of human SKPs in the step 1 can be known obtained and culturing manner in the art.

The culturing of human skin-derived precursor cells in one of embodiments of the present invention can be achieved by the following steps:

irrigating and disinfecting a skin tissue with penicillin streptomycin, cutting the skin tissue into 1 mm*2 mm tissue blocks, digesting the tissue blocks with 4° C. dispase enzyme for 12-24 hours, removing cuticle to obtain dermis; digesting the dermis with collagenase for 2-3 hours, neutralizing with fetal calf serum containing DMEM, dissociating cells and filtering the dissociated cells by a cell strainer, inoculating the filtered cells in a culture flask, adding SKPs culture, culturing the cells in 5% $CO_2$ incubator at 37° C.

The culture for SKPs, preferably, is basal culture medium with DMEM/F12=3:1, adding 2% B27, 40 ng/ml bFGF, 20 ng/ml EGF and 1% double resistant lividans.

The culturing of corneal endothelial cells B4G12 in the step 2, in one of embodiments of the present invention can be achieved by the following steps:

taking a cryopreserved tube containing B4G12 cells from ultra-low temperature freezer, moving the tube rapidly to a water bath under 37° C. to dissolve ice in the tube, transferring a suspension solution in the cryopreserved tube to a 15 mL centrifuged tube, adding 1 mL of B4G12 cell culture medium, centrifuging the solution at 1000 r/min for 5 minutes and removing the supernatant, adding 3 mL B4G12 cell culture medium again to make re-suspended cells precipitate, finally adding the cells into a culture bottle coated with 10 ug/m laminin and 10 mg/mL chondroitin sulfate, culturing the cells under normal condition and changing the solution every other day.

The culture medium for B4G12 is prepared with human endothelial cells serum free medium HE-SFM (purchased from ThermoFisher, USA) by adding 10 ng/mL bFGF.

The induction of corneal endothelial-like cells B4G12 in the step 3 comprises: inoculating the human corneal endothelial cells or B4G12 cells in a transwell chamber (upper chamber); inoculating SKPs in a culture plate (lower chamber) and co-culturing with adding the culture medium of B4G12.

The induction process of corneal endothelial-like cells in one of embodiments of the present invention comprises: coating a culture plate with 10 ug/ml laminin and 10 mg/ml chondroitin sulfate and irrigating with pbs, digesting SKPs with 0.05% pancreatic enzyme −0.02% EDTA, inoculating the digested SKPs in the culture plate, co-culturing SKPs and B4G12 using transwell chamber in manner of non-contact. The culture medium is B4G12 culture medium prepared by adding 10 ng/mL bFGF to culture medium human endothelial cells serum free medium HE-SFM. Cell morphology of part of the cells are changed to be polygon after 4 days, and the proportion of the changed cells increases with time and polygonal cells takes the majority after 8 days with the cells forming tightly connected single Mosaic arrangement with each other. The induced cells are proved to have similar morphology and marker expression by confirmation using optical microscope, immunofluorescence, real-time quantitative PCR and western blotting. The induced human corneal endothelial-like cells passage every 7 to 10 days and can stably passage 3 to 4 generations. The cells can still maintain their morphology and marker expression after passaging.

The corneal endothelial-like cells described above has the following characteristics: the cells are polygonal shape, forming tightly connected single Mosaic arrangement, and markers for expressing corneal endothelium Na+/K+ATPase and ZO-1 are all increased compared to corneal endothelial markers Na+/K+ATPase, ZO-1, N-cadherin, CA2, Col4a2 and Col8a2 of SKPs.

The corneal endothelial-like cells obtained by above method in preparation of corneal transplantation are applied as seed cells.

A corneal transplantation includes the corneal endothelial-like cell obtained by the above method.

A tissue engineering corneal posterior lamellar includes the corneal endothelial-like cell obtained by above method and a pharmacologically acceptable biodegradable material.

The pharmacologically acceptable biodegradable material comprises cornea acellular matrix etc.

The present invention has following beneficial effects.

Firstly, the present invention induces and differentiates for the first time human skin-derived precursors into the corneal endothelial-like cells, providing an effective experimental bases for human corneal reparation. At the same time, SKPs does not express HLA-DR, which inhibits the proliferation and activation of T lymphocytes. The immunogenicity and immunoreactivity of the cells are low. And skin materials are easily available and extensively source, which provides a sufficient source for corneal endothelial cells.

Secondly, the induction method utilized in the present invention, namely co-culturing of human skin-derived precursors and human corneal endothelial cell line, avoids the complex procedures to extract primary human corneal endothelial cells and avoids the problems in under-supply of human corneal donors, and avoids the production of cytotoxicity derived from chemical inducers. Furthermore, the method in the present invention has a higher induction efficiency compared with normal induction method.

Thirdly, the induction method in the present invention is simple and convenient to operate. Corneal endothelial-like cells are achieved by only one induction of the seed cells, with no other steps needed. This induction method is thus more efficient and more rapid to produce corneal endothelial-like cells than any other methods, providing a basis of industrialized production of corneal endothelial cells.

Finally, the induction method in the present invention produces corneal endothelial-like cells more like human corneal endothelial cells than those in prior art and properties of corneal endothelial-like cells is comparatively more stable. Animal model experiment prove that the corneal endothelial-like cells effectively repairs the damaged coneal endothelium.

DETAILED DESCRIPTION

Figure 1:
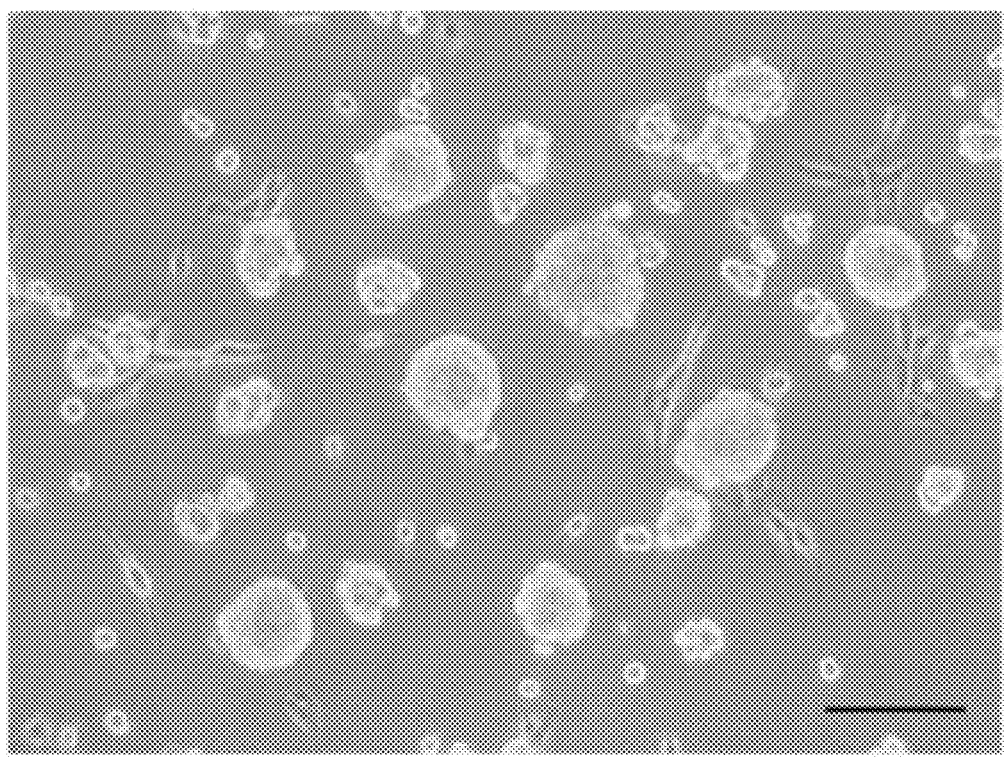
FIG. 1 shows Skin-derived Precursors (SKPs) under an optical microscope: SKPs start forming from 7 days on, spheroidal, and proliferating after 2-3 weeks, maintaining their properties after cell passage.

Embodiment 1 Induction and Differentiation of Human Skin-Derived Precursors into Corneal Endothelial-Like Cells Step 1: culturing of human Skin-derived Precursors (SKPs) comprises:

irrigating and disinfecting a skin tissue with penicillin streptomycin, cutting the skin tissue into 1 mm*2 mm tissue block, digesting the tissue with 4° C. dispase enzyme for 12-24 hours, removing cuticle to obtain dermis; digesting the dermis with collagenase for 2-3 hours, neutralizing with fetal calf serum containing DMEM, issociating cells and filtering the dissociated cells by a cell strainer, inoculating the filtered cells in a culture flask, adding SKPs culture, culturing the cells in 5% $CO_2$ incubator at 37° C. Spherical suspended SKPs are formed after about 2-3 weeks, and the cells after 2-4 generations are used for induction. The culturing observation of SKPs is shown in FIG. 1.

The culture solution for SKPs is basal culture medium of DMEM/F12=3:1, adding 2% B27, 40 ng/ml bFGF, 20 ng/ml EGF and 1% double resistant lividans.

Step 2: culturing of corneal endothelial cells B4G12 comprises:

taking a cryopreserved tube containing B4G12 cells from ultra-low temperature freezer, moving the tube rapidly to a water bath under 37° C. to dissolve the ice in the tube, transferring a suspension solution of the cryopreserved tube to a 15 mL of centrifuged tube, adding 1 mL of B4G12 cell culture medium, centrifuging the solution at 1000 r/min for 5 minutes and removing the supernatant, adding 3 mL of B4G12 culture medium again to make the re-suspended cells precipitate, finally adding the cells into a culture bottle coated with 10 ug/m laminin and 10 mg/mL chondroitin sulfate, culturing the cells under normal condition and changing the solution every other day.

The culture medium for B4G12 is prepared with human endothelial cells serum free medium HE-SFM (purchased from ThermoFisher, USA) by adding 10 ng/mL bFGF.

Step 3: induction of corneal endothelial-like cells comprises:

coating a culture plate with 10 ug/ml laminin and 10 mg/ml chondroitin sulfate and irrigating with pbs, digesting SKPs with 0.05% pancreatic enzyme –0.02% EDTA, inoculating the digested SKPs in the culture plate, co-culturing SKPs and B4G12 using transwell chamber in manner of non-contact, digesting corneal endothelial-like cells obtained by induction every 7-10 days with pancreatic enzyme-EDTA and passaging.

The transwell chamber described above (purchased from Corning, No. 3450) is mosaic chamber with diameter of 0.4 μm. Cells will not migrate from upper chamber to lower chamber, but cell excretion factors are allowed to pass through and thus inducing the cells in the lower chamber to differentiate. The chamber has a transparent thin polyester film, providing an excellent cell visibility and cell structure under phase contrast microscope.

Figure 2:
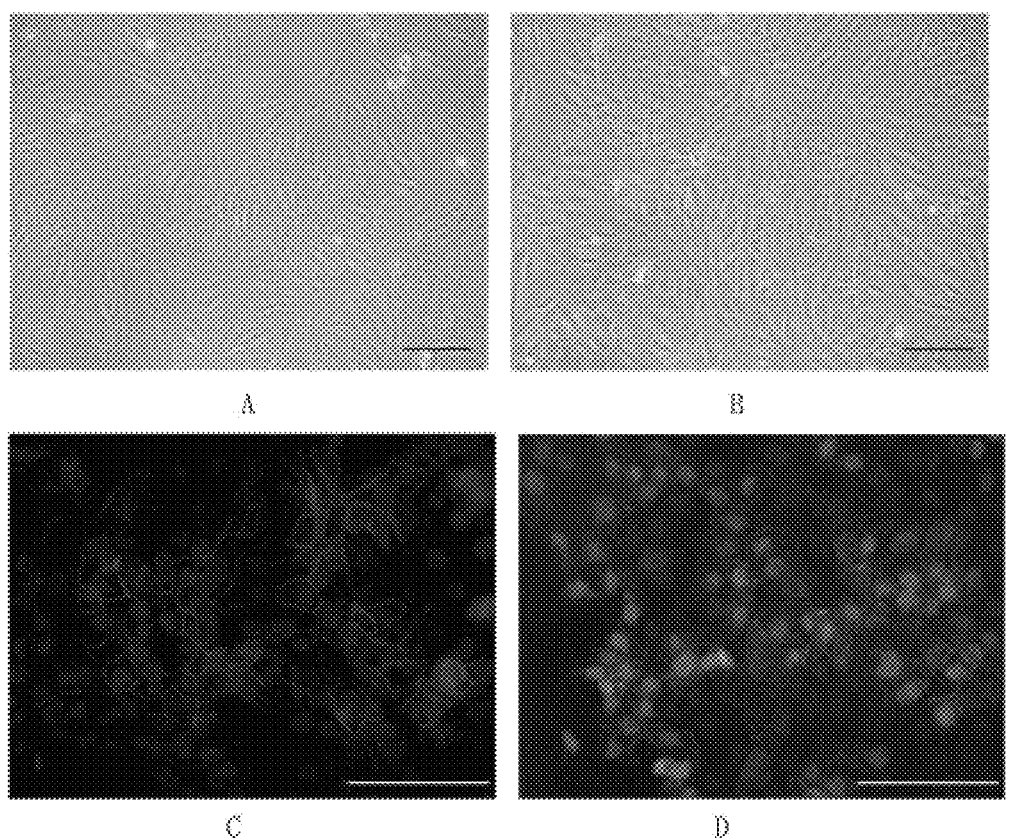
FIG. 2 shows corneal endothelial-like cells induced and differentiated by SKPs under an optical microscope. A: part of the cells start to be polygonal after 4 days of induction; B: majority of the cells are polygonal after 8 days, tightly connected single Mosaic arrangement are formed with each other; C and D: induced cell express markers for corneal endothelium, namely Na+/K+ATPase and ZO-1.
Figure 3:
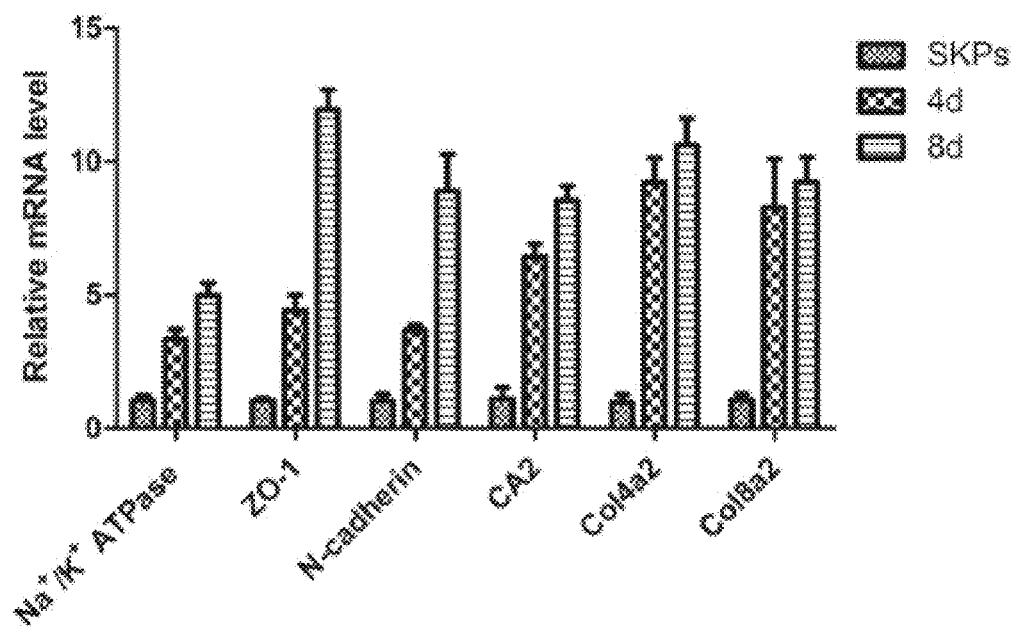
FIG. 3 shows the detection results of corneal endothelial-like cells by RT-PCR, showing different degrees of enhanced expression of markers in corneal endothelial-like cells compared to that of SKPs.
Figure 4:
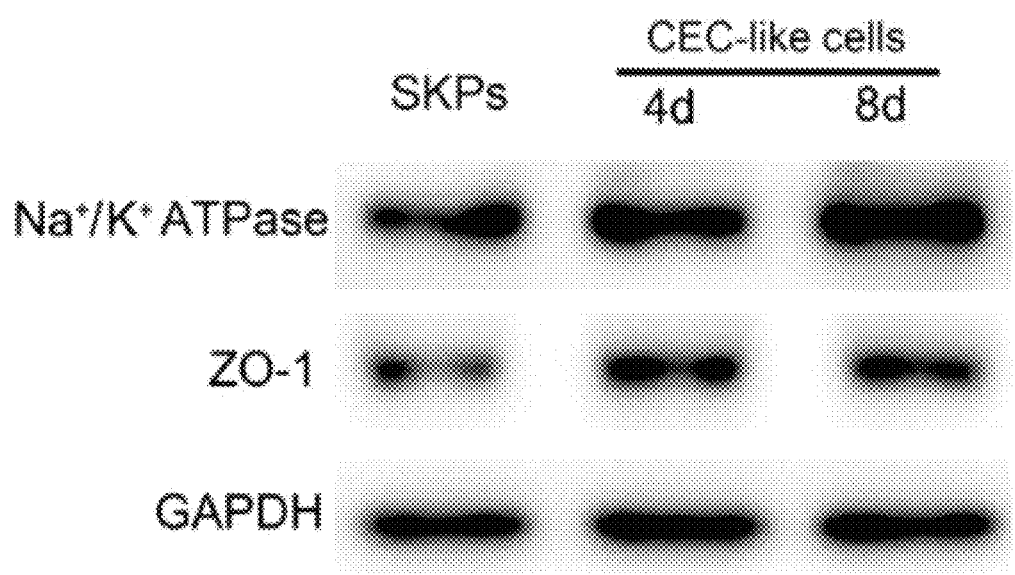
FIG. 4 shows the detection results of corneal endothelial-like cells by Western blotting, showing an enhanced expression of Na+/K+ATPase and ZO-1 in corneal endothelial-like cells compared with SKPs.
Figure 5:
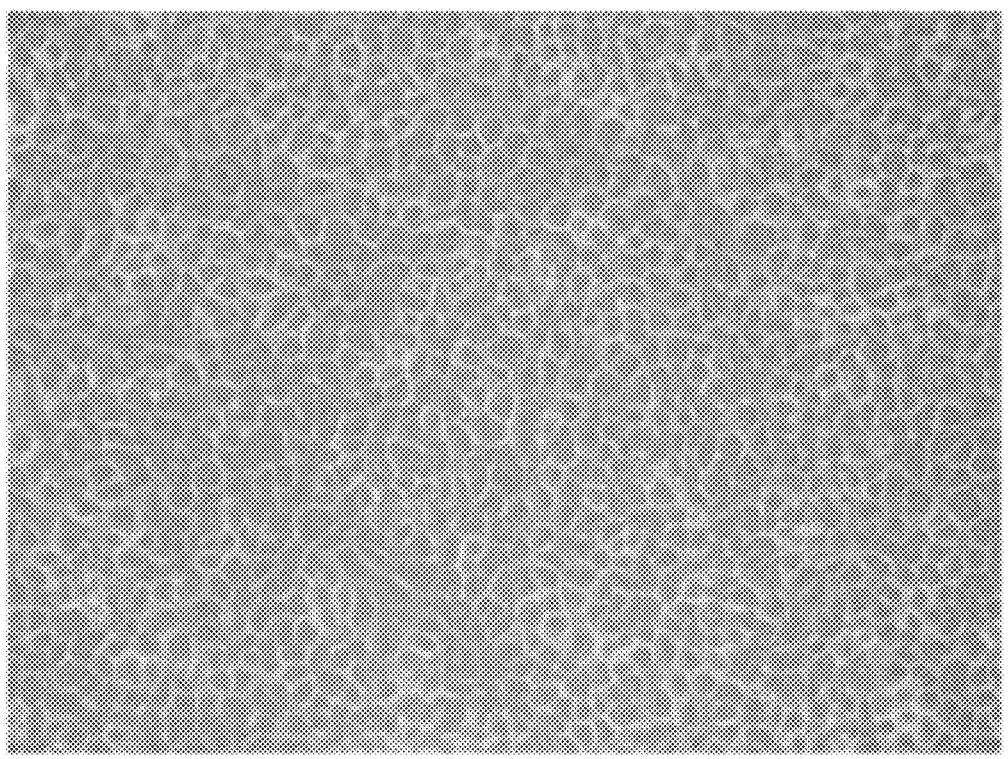
FIG. 5 shows the cell passage culturing of corneal endothelial-like cells under an optical microscope: cells are still single-layer polygonal.

Embodiment 2 Identification of Corneal Endothelial-Like Cells and Corneal Reparative Experiment Cell morphology of part of the cells are changed to be polygon after 4 days, and the proportion of the changed cells increases with time and polygonal cells takes the majority after 8 days with the cells forming tightly connected single Mosaic arrangement with each other. The induced cells are proved to have similar morphology and marker expression by confirmation using optical microscope, immunofluorescence, real-time quantitative PCR and western blotting. The induced human corneal endothelial-like cells passage every 7 to 10 days and can stably passage 3 to 4 generations. The cells can still maintain their morphology and marker expression after passaging. FIG. 2 refers to a picture of induced corneal endothelial-like cells under optical microscope. FIG. 3 and FIG. 4 refer to results respectively detected by RT-PCR and by western blotting.

Rabbit corneal endothelial transplantation experiment comprises the following procedures. Firstly, intravenous anesthesia of New Zealand rabbit was done with pentobarbital sodium, followed by normal disinfection, topical anesthesia was performed by Benoxil, conjunctival sac was irrigated with disinfected saline solution and lidocaine was retrobulbar injected. Then a scleral tunnel was made under the operating microscope, and paracentesis of the anterior chamber was done followed by injection of viscoelastics. Then corneal endothelium was abrased and the corneal endothelial-like cells are transplanted at a density of 3000/$mm^2$ into the anterior chamber, closing the scleral tunnel in the end. The operated eye should be kept in down position for 6 hours after the operation. Tobramycin and Dexamethasone Ophthalmic Ointment as well as Ofloxacin Eye Ointment are used in the operated eye. Inspection with slitlamp, confocal laser scanning microscopy, AC-OCT and etc. are periodically performed. The dead corneal cells are periodically taken to be inspected with fluorescence microscope, HE stain and etc.

Figure 6:
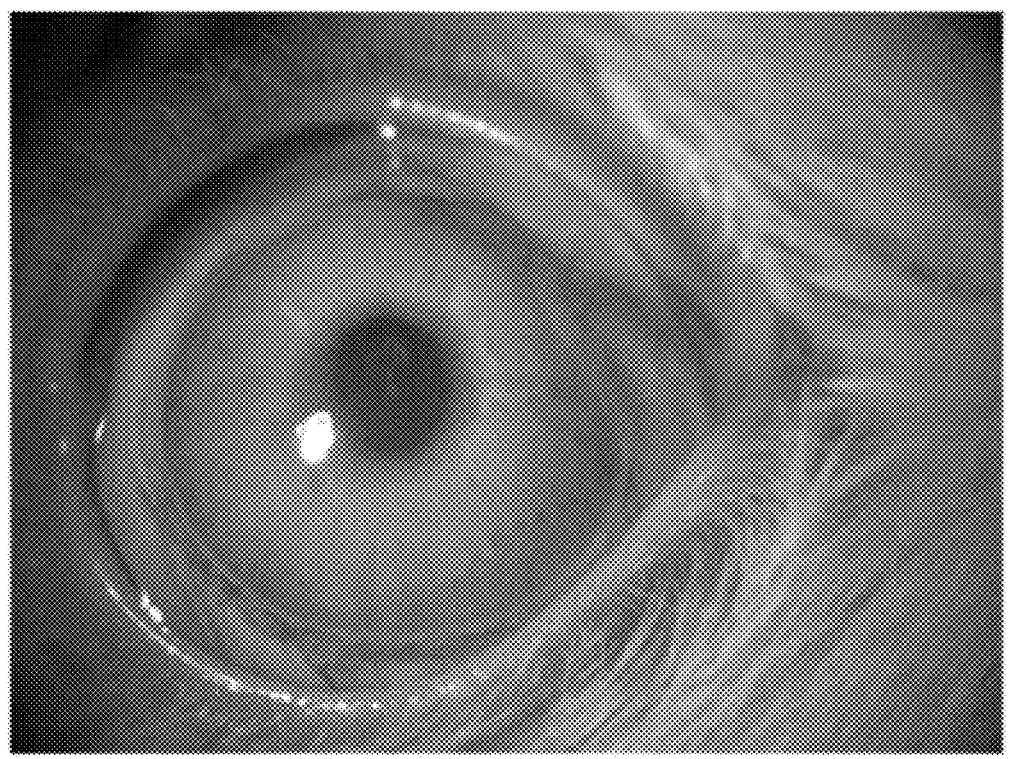
FIG. 6 shows the experimental result picture of rabbit corneal endothelial transplantation: corneal transparency is increased gradually after transplantation and cornea is almost completely transparent at 7 days after transplantation.
Figure 7:
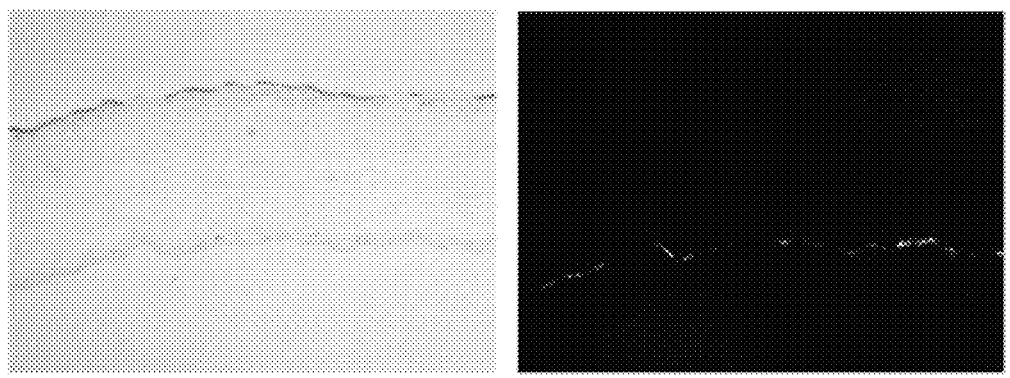
FIG. 7 shows a frozen section of dead cornea and a picture detected by fluorescence microscope after corneal turning transparent and after corneal endothelial transplantation. Corneal posterior surface in the corneal endothelial-like cells is coated with single layer of Dil-stain. A shows the cornea frozen section and B shows the picture detected by fluorescence microscope.

The animal experiment shows that opacification of the rabbit cornea is gradually mitigated, with thickness of cornea gradually decreased. The cornea is almost completely transparent at 7 days after the transplantation (see FIG. 6). There are single-layered tightly-arranged polygonal corneal endothelial-like cells in corneal descemet membrane. Red fluorescence cells are seen and Na+/K+ATPase are expressed. While in the comparison group, no endothelial cells are found in corneal descemet membrane, with no red fluorescence been found.

The embodiments described above are only the description of preferred embodiments of the present invention, but not limitation of the scope of the present invention. Any changes or improvement made by people having ordinary skill in the art within spirit of the present invention shall be included in the protection scope of the present invention.

What is claimed is:

1. A method of producing corneal endothelial-like cells, comprising:
    co-culturing human skin-derived precursors (SKPs) and B4G12 cell line in a human endothelial serum free medium (HE-SFM) with 10 ng/mL bFGF in a non-contact manner so as to induce the SKPs to differentiate into corneal endothelial-like cells.

2. The method of claim 1, wherein the step of co-culturing human SKPs and B4G12 cell line in a human endothelial serum free medium (HE-SFM) with 10 ng/mL bFGF in a non-contact manner further comprises:
    inoculating the B4G12 cell line in a transwell chamber (upper chamber);
    coating a culture plate with 10 μg/ml laminin and 10 mg/ml chondroitin sulfate and irrigating with phosphate buffered saline (pbs);
    digesting the SKPs with 0.05% pancreatic enzyme-0.02% EDTA; and
    inoculating the digested SKPs in the coated culture plate (lower chamber).

3. The method of claim 2, wherein the corneal endothelial-like cells obtained is capable of passaging to passage 3-4.

4. The method of claim 1, further comprising a step of culturing the human SKPs, comprising:
    irrigating and disinfecting a skin tissue with penicillin streptomycin and cutting the skin tissue into tissue blocks;
    digesting the tissue blocks with dispase enzyme at 4° C. for 12-24 hours and removing cuticle to obtain dermis;
    digesting the dermis with collagenase for 2-3 hours and neutralizing with fetal calf serum containing DMEM; and
    dissociating cells and filtering the dissociated cells, inoculating the filtered cells in a culture flask, culturing the cells in 5% CO2 incubator at 37° C. until formation of spherical suspended SKPs, and passaging to obtain SKPs for differentiation.

5. The method of claim 1, further comprising a step of culturing the B4G12 cell line, comprising:
    unfreezing cryopreserved B4G12 cell line in a water bath at 37° C. to form a suspension solution, and transferring the suspension solution to a 15 mL centrifuged tube;
    adding 1 mL of HE-SFM to the centrifuged tube, centrifuging the suspension solution at 1000 r/min for 5 min to produce a supernatant and a precipitate;
    discarding the supernatant and adding 3 mL of HE-SFM again to re-suspend the precipitate; and
    adding the re-suspended cells into a culture bottle coated with 10 μg/ml aminin and 10 mg/ml chondroitin sulfate to culture the B4G12 cell line, wherein culture solution is changed every other day.

* * * * *